(12) United States Patent
Gurley et al.

(10) Patent No.: US 7,402,604 B2
(45) Date of Patent: Jul. 22, 2008

(54) POSITIVE MODULATORS OF NICOTINIC RECEPTOR AGONISTS

(75) Inventors: David Gurley, Wilmington, DE (US); James Rosamond, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 218 days.

(21) Appl. No.: 11/178,668

(22) Filed: Jul. 11, 2005

(65) Prior Publication Data

US 2005/0245595 A1 Nov. 3, 2005

Related U.S. Application Data

(62) Division of application No. 10/111,029, filed as application No. PCT/SE00/02147 on Nov. 1, 2000, now Pat. No. 7,064,143.

(30) Foreign Application Priority Data

Nov. 3, 1999 (SE) .................. 9903998

(51) Int. Cl.
*A61K 31/405* (2006.01)
*C07D 209/42* (2006.01)

(52) U.S. Cl. .................. 514/419; 548/492

(58) Field of Classification Search .............. 514/419; 548/492
See application file for complete search history.

(56) References Cited

U.S. PATENT DOCUMENTS 5,690,697 A 11/1997 Samain
6,750,242 B1 * 6/2004 Gurley et al. ............... 514/414

FOREIGN PATENT DOCUMENTS

| EP | 0237781 A2 | 9/1987 |
|----|------------|--------|
| EP | 0722941 | 7/1996 |
| GB | 1310235 A | 3/1973 |
| WO | WO 9205170 A1 | 4/1992 |
| WO | WO 9311106 A1 | 6/1993 |
| WO | WO 9318026 A1 | 9/1993 |
| WO | WO 9530655 | 11/1995 |

OTHER PUBLICATIONS

Phytochemistry, vol. 11, 1972, Torigoe, et al. "Cytokinin Activity of Azaindene . . . and Indole Derivatives", pp. 1623-1630, see cmpds (XIII & (XIV), p. 1625.
Chem Abstracts, vol. 57, (Columbus, Ohio, USA), Piers et al. "The Synthesis of Mercaptoindoles", Abst No. 15053h, Can. J. Chem. 1962, 40, 511-517.
Goodman & Gilman's, "The Pharmaceutical Basis of Therapeutics," 10th Edition, 2001, p. 549.

* cited by examiner

Primary Examiner—Kamal A Saeed
(74) Attorney, Agent, or Firm—Kenneth F. Mitchell

(57) ABSTRACT

Compounds according to formula I:

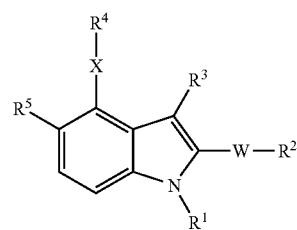

wherein $R^1$, W, $R^2$, $R^3$, X, $R^4$ and $R^5$ are as described in the specification, enantiomers thereof, pharmaceutically acceptable salts thereof, processes for preparing them, pharmaceutical compositions containing them and their use in therapy, especially for treatment of conditions associated with reductions in nicotinic transmission.

8 Claims, No Drawings

POSITIVE MODULATORS OF NICOTINIC RECEPTOR AGONISTS

RELATED APPLICATIONS

This Application is a Divisional of U.S. application Ser. No. 10/111,029, filed Apr. 18, 2002, now U.S. Pat. No. 7,064,143, which is the National Phase of PCT/SE00/02147, filed Nov. 1, 2000.

FIELD OF THE INVENTION

The present invention relates to novel compounds or pharmaceutically acceptable salts thereof, processes for preparing them, pharmaceutical compositions containing them and their use in therapy. The novel compounds referred to are positive modulators of nicotinic receptor agonists, said positive modulator having the capability to increase the efficacy of the said nicotinic receptor agonists.

BACKGROUND OF THE INVENTION

Cholinergic receptors normally bind the endogenous neurotransmitter acetylcholine (ACh), thereby triggering the opening of ion channels. ACh receptors in the mammalian central nervous system can be divided into muscarinic (mAChR) and nicotinic (nAChR) subtypes based on the agonist activities of muscarine and nicotine, respectively. The nicotinic acetylcholine receptors are ligand-gated ion-channels containing five subunits (for reviews, see Colquhon et al. (1997) Advances in Pharmacology 39, 191-220; Williams et al. (1994) Drug News & Perspectives 7, 205-223; Doherty et al. (1995) Annual reports in Medicinal Chemistry 30, 41-50). Members of the nAChR gene family have been divided into two groups based on their sequences; members of one group are considered β subunits, while a second group are classified as α subunits (for reviews, see Karlin & Akabas (1995) Neuron 15, 1231-1244; Sargent (1993) Annu. Rev. Neurosci. 16, 403-443). Three of the α subunits, α7, α8 and α9, form functional receptors when expressed alone and thus presumably form homooligomeric receptors.

An allosteric transition state model of the nAChR involves at least a resting state, an activated state and a "desensitized" closed channel state (Williams et al., supra; Karlin & Akabas, supra). Different nAChR ligands can thus differentially stabilize the conformational state to which they preferentially bind. For example, the agonists ACh and (−)-nicotine stabilize the active and desensitized states.

Changes of the activity of nicotinic receptors has been implicated in a number of diseases. Some of these, e.g. myasthenia gravis and ADNFLE (autosomal dominant nocturnal front lobe epilepsy) (Kuryatov et al. (1997) J. Neurosci. 17(23):9035-47), are associated with reductions in the activity of nicotinic transmission either through a decrease in receptor number or increased desensitization, a process by which receptors become insensitive to the agonist. Reductions in nicotinic receptors have also been hypothesized to mediate cognitive deficits seen in diseases such as Alzheimer's disease and schizophrenia (Williams et al., supra). The effects of nicotine from tobacco are also mediated by nicotinic receptors. Increased activity of nicotinic receptors may reduce the desire to smoke.

The use of compounds which bind nicotinic acetylcholine receptors in the treatment of a range of disorders involving reduced cholinergic function such as Alzheimer's disease, cognitive or attention disorders, attention deficit hyperactivity disorders, anxiety, depression, smoking cessation, neuroprotection, schizophrenia, analgesia, Tourette's syndrome, and Parkinson's disease has been discussed in McDonald et al. (1995) "Nicotinic Acetylcholine Receptors: Molecular Biology, Chemistry and Pharmacology", Chapter 5 in Annual Reports in Medicinal Chemistry, vol. 30, pp. 41-50, Academic Press Inc., San Diego, Calif.; and in Williams et al., supra.

However, treatment with nicotinic receptor agonists which act at the same site as ACh is problematic because ACh not only activates, but also blocks receptor activity through processes which include desensitization (for a review, see Ochoa et al. (1989) Cellular and Molecular Neurobiology 9, 141-178) and uncompetitive blockade (open-channel block); Forman & Miller (1988) Biophysical Journal 54(1):149-58. Furthermore, prolonged activation appears to induce a long-lasting inactivation. Therefore agonists of ACh can be expected to reduce activity as well as enhance it. At nicotinic receptors in general, and, of particular note, at the α7-nicotinic receptor, desensitization limits the duration of current during agonist application.

DISCLOSURE OF THE INVENTION

It has surprisingly been found that certain compounds can enhance the efficacy of agonists at nicotinic receptors. It is believed that compounds having this type of action (hereinafter referred to as "positive modulators") will be particularly useful for treatment of conditions associated with reductions in nicotinic transmission. In a therapeutic setting such compounds could restore normal interneuronal communication without affecting the temporal profile of activation. In addition, they would not produce long-term inactivation as prolonged application of agonist may.

According to the invention it has been found that compounds of Formula I:

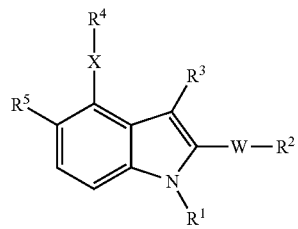

wherein:

$R^1$ represents hydrogen, $C_1$-$C_4$ alkyl, $C_2$-$C_4$ alkenyl, $C_2$-$C_4$ alkynyl, or $(CH_2)_n Ar$;

W represents $C(O)$, $C(O)O$, $C(O)NR^6$, or a bond;

$R^2$ represents hydrogen, Ar, or $(CH_2)_p CH[(CH_2)_q R^7](CH_2)_r R^8$; or together $R^2$ and $R^6$ represent $(CH_2)_j Y(CH_2)_k$;

$R^3$ and $R^5$ independently represent hydrogen, halogen, or $C_1$-$C_4$ alkyl;

X represents oxygen, or NH;

$R^4$ represents hydrogen, $C_1$-$C_4$ alkyl, $(CH_2)_u Ar$, $R^9 CO$, or $R^9 SO_2$;

$R^6$ represents hydrogen, $C_1$-$C_4$ alkyl, aryl, or heteroaryl; or together $R^2$ and $R^6$ represent $(CH_2)_j Y(CH_2)_k$;

$R^7$ and $R^8$ independently represent hydrogen, halogen, CN, $N_3$, $CF_3$, $NO_2$, Ar, $OR^{10}$, $NR^{10}R^{11}$, $C(O)OR^{10}$, $OC(O)R^{10}$, $C(O)NR^{10}R^{11}$, $NR^{10}C(O)R^{11}$, $SO_2NR^{10}R^{11}$, $rNR^{10}SO_2R^{11}$;

$R^9$ represents $C_1$-$C_4$ alkyl, or Ar;

Ar represents phenyl, naphthyl, or a 5- or 6-membered heterocyclic ring containing 0-3 nitrogens, 0-1 sulfurs and 0-1 oxygens;

Ar is optionally substituted with one or more substituents independently selected from: hydrogen, halogen, $C_1$-$C_4$ alkyl, $C_2$-$C_4$ alkenyl, $C_2$-$C_4$ alkynyl, $(CH_2)_n$aryl, CN, $NO_2$, $CF_3$, $OR^{12}$, $NR^{12}R^{13}$ and $COOR^{12}$;

$R^{10}$, $R^{11}$, $R^{12}$ and $R^{13}$ independently represent hydrogen, $C_1$-$C_4$ alkyl, aryl, or heteroaryl; or together $R^{10}$ and $R^{11}$ and/or $R^{12}$ and $R^{13}$ independently represent $(CH_2)_jY(CH_2)_k$;

Y represents oxygen, sulfur, $NR^{14}$, or a bond;

j is 2-4;

k, m, n, p, q, t, and u are independently 0-2;

$R^{14}$ represents hydrogen, $C_1$-$C_4$ alkyl, aryl or heteroaryl; or an enantiomer thereof, and pharmaceutically acceptable salts thereof, enhance the efficacy of agonists at nicotinic receptors.

Preferred compounds of the invention are compounds of Formula I, wherein;

$R^4$ represents hydrogen, methyl, or benzyl;

$R^1$ represents hydrogen, or methyl;

$R^3$ and $R^5$ independently represent hydrogen;

W represents a bond;

X represents oxygen;

$R^2$ represents hydrogen, methyl; (4-benzyl)oxazolin-2-yl, or A;

A represents $COOR^{15}$, or $CONR^{16}R^{17}$;

$R^{15}$ represents hydrogen, or $CH_2CH_3$;

$R^{16}$ represents hydrogen, or $C_1$-$C_4$ alkyl;

$R^{17}$ represents $C_1$-$C_4$ alkyl, $(CH_2)_n$-phenyl-Y, or $CHR^{18}CHR^{19}$-Z;

$R^{18}$ represents hydrogen, phenyl, or benzyl;

$R^{19}$ represents hydrogen, or benzyl;

$R^{20}$ represents benzyl;

Y represents hydrogen, Cl, $N(CH_3)_2$, or phenyl;

Z represents Cl, OH, F, $N_3$, or $NH_2$;

n is 0-4;

or an enantiomer thereof, and pharmaceutically acceptable salts thereof.

Preferred compounds of the invention include the following:

Ethyl 4-hydroxy-1-methyl-1H-indole-2-carboxylate;
4-Hydroxy-1-methyl-1H-indole-2-carboxylic acid;
N-Phenethyl 4-hydroxy-1-methyl-1H-indole-2-carboxamide;
N-Methyl-N-Phenethyl 4-hydroxy-1-methyl-1H-indole-2-carboxamide;
N-(4-Dimethylaminobenzyl) 4-hydroxy-1-methyl-1H-indole-2-carboxamide;
N-(4-Chlorobenzyl) 4-hydroxy-1-methyl-1H-indole-2-carboxamide;
N-Benzyl 4-hydroxy-1-methyl-1H-indole-2-carboxamide;
N-(4-Phenylbutyl) 4-hydroxy-1-methyl-1H-indole-2-carboxamide;
N-(3-Phenylpropyl) 4-hydroxy-1-methyl-1H-indole-2-carboxamide;
N-Phenyl 4-hydroxy-1-methyl-1H-indole-2-carboxamide;
N-(4-Chlorophenyl) 4-hydroxy-1-methyl-1H-indole-2-carboxamide;
N-(3-Biphenyl) 4-hydroxy-1-methyl-1H-indole-2-carboxamide;
N-Ethyl 4-hydroxy-1-methyl-1H-indole-2-carboxamide;
4-Hydroxy-1-methyl-2-(pyrrolidin-1-ylcarbonyl)-1H-indole;
N-(1-Fluoromethyl-2-phenylethyl) 4-hydroxy-1-methyl-1H-indole-2-carboxamide;
(R)-N-(2-Hydroxy-1-phenylethyl) 4-hydroxy-1-methyl-1H-indole-2-carboxamide;
(S)-N-(2-Azido-1-benzylethyl)-4-hydroxy-1-methyl-1H-indole-2-carboxamide;
N-(2-Fluoroethyl)-4-hydroxy-1-methyl-1H-indole-2-carboxamide;
(R)-N-(2-Fluoro-3-phenylpropyl)-4-hydroxy-1-methyl-1H-indole-2-carboxamide;

or an enantiomer thereof, and pharmaceutically acceptable salts thereof.

Unless otherwise indicated, the $C_1$-$C_4$ alkyl groups referred to herein, e.g., methyl, ethyl, n-propyl, n-butyl, i-propyl, i-butyl, t-butyl, s-butyl, may be straight-chained or branched, and the $C_3$-$C_4$ alkyl groups may also be cyclic, e.g., cyclopropyl, cyclobutyl.

Unless otherwise indicated, the $C_2$-$C_4$ alkenyl groups referred to herein may contain one or two double bonds, e.g., ethenyl, i-propenyl, n-butenyl, i-butenyl, allyl, 1,3-butadienyl.

Unless otherwise indicated, the $C_2$-$C_4$ alkynyl groups referred to herein contain one triple bond, e.g., ethynyl, propynyl, 1- or 2-butynyl.

Halogen referred to herein may be fluoride, chloride, bromide, or iodide. The compounds of the invention have the advantage that they may be less toxic, be more efficaous, be longer acting, have a broader range of activity, be more potent, produce fewer side effects, are more easily absorbed or have other useful pharmacological properties.

Methods of preparation

In the reaction schemes and text that follow $R^1$, $R^2$, $R^3$, $R^4$, $R^5$, W, and X, unless otherwise indicated, are as defined above for formula I. The compounds of formula I may be prepared according to the methods outlined in Schemes I, II and III.

Scheme I outlines general methods for the preparation of compounds of formula I wherein $XR^4$ represents OH and W represents $CONR^6$ (formula IIa), COO (formula IXa) or CO (formula XIIa) from a common intermediate of formula Va wherein $XR^4$ represents OBn (Bn referring to benzyl), W represents COO, and $R^2$ represents hydrogen. The other substituents, $R^1$, $R^3$ and $R^5$, are as defined for formula I.

Scheme I

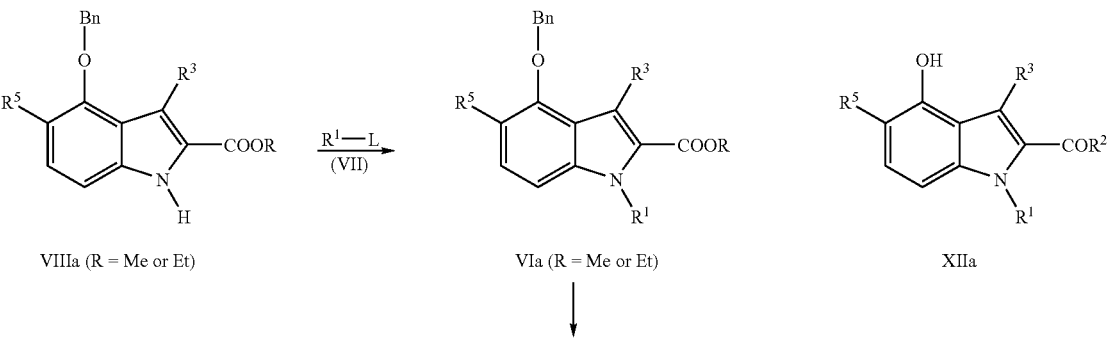

VIIIa (R = Me or Et)　　VIa (R = Me or Et)　　XIIa

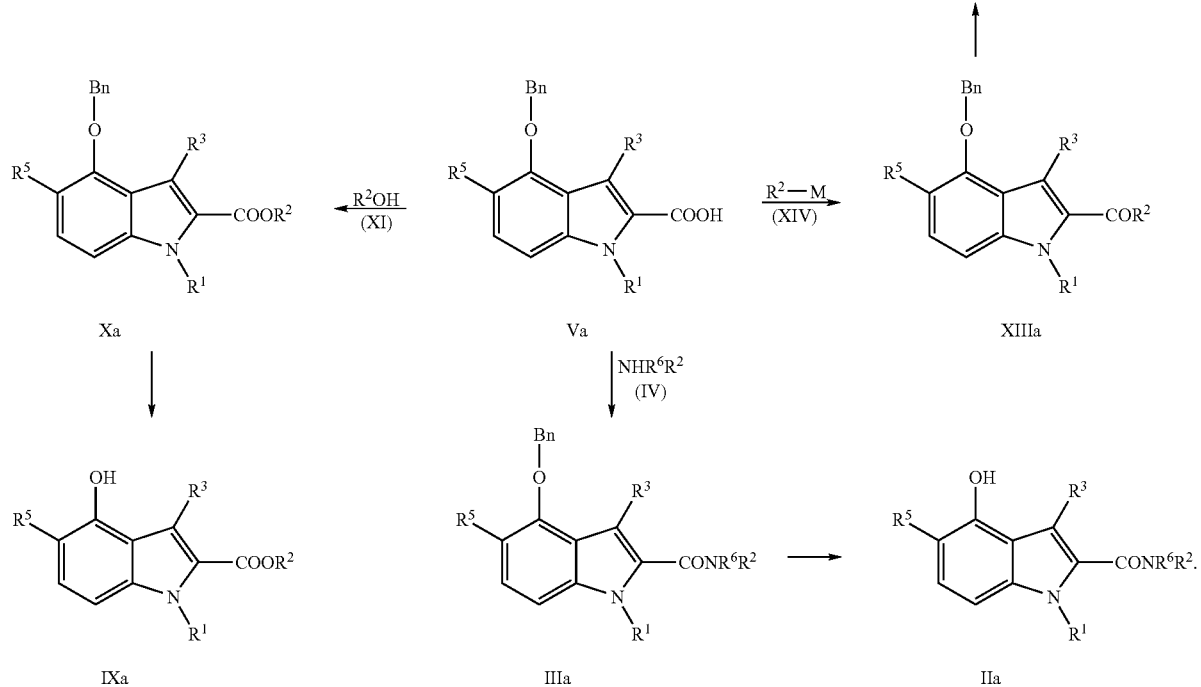

Compounds of formula IIa may be prepared from compounds of formula IIIa, representing compounds of formula I wherein $XR^4$ represents OBn and W represents $CONR^6$, by catalytic hydrogenation with a suitable hydrogen source in a suitable solvent. Suitable catalysts include palladium black and palladium on charcoal. Suitable hydrogen sources include hydrogen gas and 1,4-cyclohexadiene. Suitable solvents include ethanol (EtOH), ethyl acetate (EtOAc), water, and tetrahydrofuran (THF). The reaction is preferably performed at a temperature of 20-50° C., a pressure of 1-4 atmospheres and most preferably at ambient temperature and pressure with 1,4-cyclohexadiene or at ambient temperature and a pressure of 3 atmospheres with hydrogen gas.

Compounds of formula IIIa may be prepared from compounds of formula Va, representing compounds of formula I wherein $XR^4$ represents OBn, W represents COO, and $R^2$ represents hydrogen, by reaction with a compound of formula IV, wherein $R^2$ and $R^6$ are as defined for formula I, in the presence of an amide bond forming agent in a suitable solvent. Suitable amide bond forming agents include (a) carbodiimides such as dicyclohexylcarbodiimide and diisopropylcarbodiimide, (b) carbodiimides with additives such as 1-hydroxybenzotriazole (HOBt) and N-hydroxy succinimide (HOSu), and (c) phosphonium and uronium salts such as BOP, PyBOP, HBTU, and TBTU (benzotriazole-1-yloxytris(dimethylamino)phosphonium hexafluorophosphate, benzotriazole-1-yloxytrispyrrolidinophosphonium hexafluorophosphate, 2-(1H-benzotriazole-1-yl)-1,1,3,3-tetrametyluronium hexafluorophosphate, and 2-(1H-benzotriazole-1-yl)-1,1,3,3-tetrametyluronium tetrafluoroborate; respectively) in the presence of a suitable tertiary amine base such as N,N-diisopropylethylamine (DIEA) or triethylamine (TEA). Suitable solvents include N,N-dimethylformamide (DMF), N-methylpyrrolidone (NMP), trifluoroethanol (TFE), acetonitrile (ACN), THF, dichloromethane (DCM), chloroform and EtOAc. The reaction is preferably performed at a temperature of 0-50° C. and most preferably at ambient temperature. Alternatively, compounds of formula IIIa may be prepared from compounds of formula Va by reaction with an acid chloride forming agent such as thionyl chloride ($SOCl_2$) followed by reaction with a compound of formula IV in the presence of a suitable base and solvent. Compounds of formula IV are either commercially available or may be prepared by methods known to one skilled in the art.

Alternatively, compounds of formula IIa may be prepared sequentially from compounds of formula Va by (1) reductive cleavage of the benzyl group by the method described two paragraphs above, (2) carboxyl activation over 5-30 minutes with amide bond forming agents a or b as described in the paragraph above; and (3) amidation with compounds of formula IV. The reaction conditions are in accordance with those described in the preceding two paragraphs.

Compounds of formula Va may be prepared from compounds of formula VIa, representing compounds of formula I wherein $XR^4$ represents OBn, W represents COO, and $R^2$ represents R which is methyl or ethyl, by hydrolysis with a suitable base in a suitable solvent. Suitable bases include sodium hydroxide (NaOH), potassium hydroxide (KOH), lithium hydroxide (LiOH) and cesium hydroxide (CsOH). Suitable solvents include aqueous MeOH, aqueous EtOH and aqueous THF. The reaction is preferably performed at a temperature of 0-50° C. and most preferably at ambient temperature.

Compounds of formula VIa may be prepared from compounds of formula VIIIa, representing compounds of formula I wherein $R^1$ represents hydrogen, $XR^4$ represents OBn, W represents COO, and $R^2$ represents R which is methyl or ethyl, by reaction in a suitable solvent with a suitable base followed by treatment with a compound of formula VII, wherein $R^1$ is defined as in formula I and L is a suitable leaving group. Suitable bases include sodium hydride (NaH), potassium hydride (KH), potassium tert-butoxide (KOtBu), lithium diisopropylamide (LDA), lithium hexamethyldisilazide (LHMDA) and sodium amide (NaNH$_2$). Suitable leaving groups include halogen, triflate (TfO), methanesulfonate (MsO) and p-toluenesulfonate (pTsO). Suitable solvents for the reaction include DMF, NMP, ACN, and THF. The reaction is preferably performed at a temperature of 0-50° C. and most preferably at ambient temperature. Compounds of formula VII and VIIIa are either commercially available or may be prepared by methods known to one skilled in the art.

Compounds of formula IXa may be prepared from compounds of formula Xa, representing compounds of formula I wherein XR$^4$ represents OBn and W represents COO, according to an analogous procedure described for the preparation of compounds of formula IIa.

Compounds of formula Xa may be prepared from compounds of formula Va, representing compounds of formula I wherein XR$^4$ represents OBn, W represents COO, and R$^2$ represents hydrogen, by reaction with an acid chloride forming agent such as SOCl$_2$ followed by reaction with an alcohol of formula XI, wherein R$^2$ is as defined for formula I, in the presence of a suitable base and solvent. Suitable bases include DIEA, TEA, pyridine, sodium bicarbonate (NaHCO$_3$) and sodium carbonate (Na$_2$CO$_3$). Suitable solvents include THF, DCM, chloroform, benzene, toluene and EtOAc. The reaction is preferably performed at a temperature of 0-100° C. and most preferably at ambient temperature while the prior acid chloride forming step is preferably performed in a refluxing solvent such as benzene, chloroform or neat SOCl$_2$. Alcohols of formula XI are either commercially available or may be prepared by methods known to one skilled in the art.

Compounds of formula XIIa may be prepared from compounds of formula XIIIa, representing compounds of formula I wherein XR$^4$ represents OBn and W represents CO, according to an analogous procedure described for the preparation of compounds of formula IIa.

Compounds of formula XIIIa may be prepared from compounds of formula Va, representing compounds of formula I wherein XR$^4$ represents OBn, W represents COO, and R$^2$ represents hydrogen, by reaction in a suitable solvent with an organometallic compound of formula XIV, wherein R$^2$ is as defined for formula I and M represents a metal such as magnesium or preferably lithium. Suitable solvents include ether, 1,2-dimethoxyethane, THF and 1,4-dioxane. The reaction is preferably performed at a temperature of 0-100° C. and most preferably at a temperature of 25-60° C. Organometallic compounds of formula XIV are either commercially available or may be prepared by methods known to one skilled in the art.

Scheme II outlines general methods for the preparation of compounds of formula I wherein XR$^4$ represents NH$_2$ and W represents CONR$^6$ (formula IIb), COO (formula IXb) or CO (formula XIIb) from a common intermediate of formula Vb wherein XR$^4$ represents NO$_2$, W represents COO, and R$^2$ represents hydrogen. The other substituents, R$^1$, R$^3$ and R$^5$, are as defined for formula I.

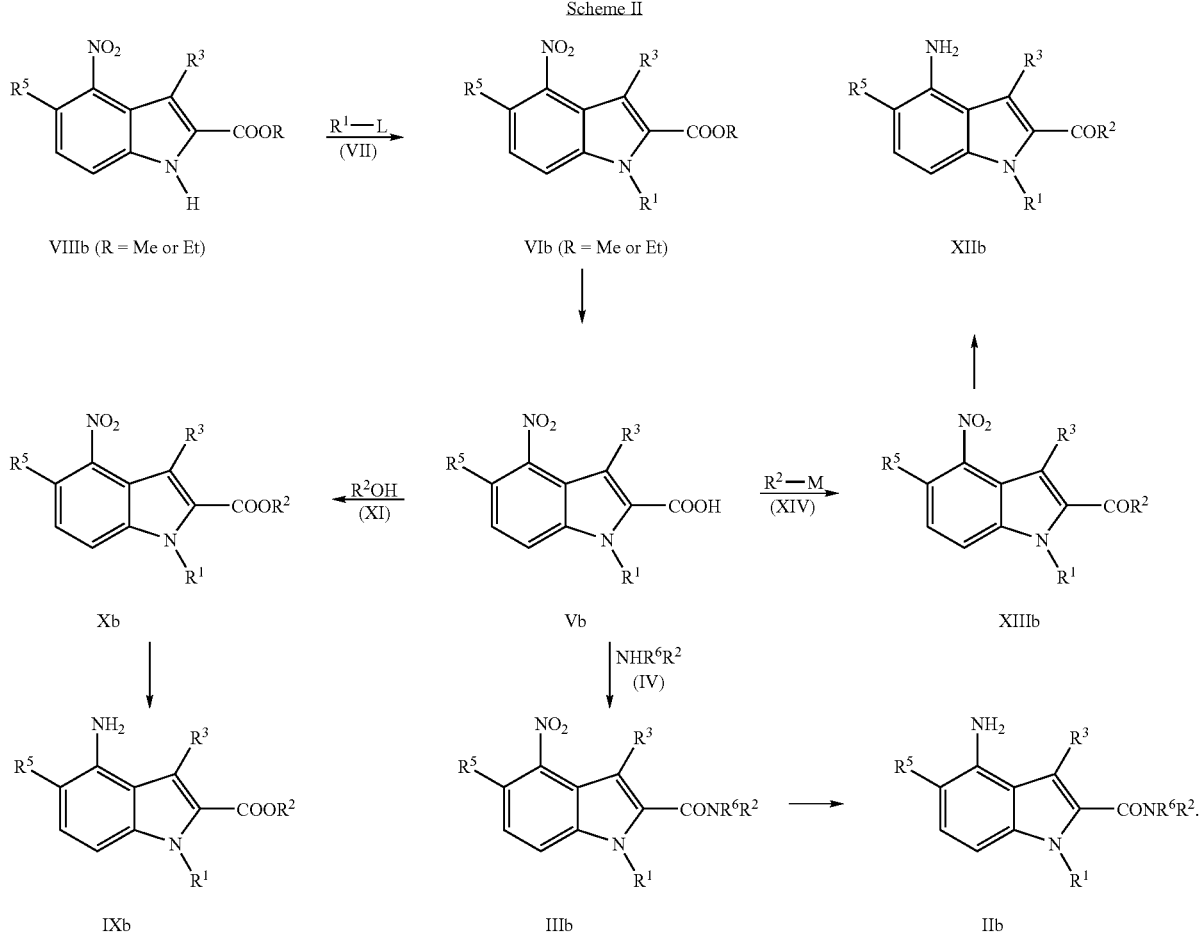

Compounds of formula IIb may be prepared from compounds of formula IIIb, representing compounds of formula I wherein $XR^4$ represents $NO_2$ and W represents $CONR^6$, by reaction with a suitable reducing agent in a suitable solvent. Suitable reducing agents include hydrogen gas with palladium on charcoal, zinc dust with acetic acid (HOAc) or hydrochloric acid (HCl), or iron powder with HOAc. Suitable solvents and cosolvents include EtOH, HOAc and water. The reaction is preferably performed at a temperature of 25-120° C.

Compounds of formula IIIb may be prepared from compounds of formula Vb, representing compounds of formula I wherein $XR^4$ represents $NO_2$, W represents COO, and $R^2$ represents hydrogen, by reaction with a compound of formula IV, wherein $R^2$ and $R^6$ are as defined for formula I, according to an analogous procedure described for the preparation of compounds of formula IIIa.

Compounds of formula Vb may be prepared from compounds of formula VIb, representing compounds of formula I wherein $XR^4$ represents $NO_2$, W represents COO, and $R^2$ represents R which is methyl or ethyl, according to an analogous procedure described for the preparation of compounds of formula Va.

Compounds of formula VIb may be prepared from compounds of formula VIIIb, representing compounds of formula I wherein $R^1$ represents hydrogen, $XR^4$ represents $NO_2$, W represents COO, and $R^2$ represents R which is methyl or ethyl, by reaction in a suitable solvent with a suitable base followed by treatment with a compound of formula VII, wherein $R^1$ is defined as in formula I and L is a suitable leaving group, according to an analogous procedure described for the preparation of compounds of formula VIa. Compounds of formula VIIIb are either commercially available or may be prepared by methods known to one skilled in the art.

Compounds of formula IXb may be prepared from compounds of formula Xb, representing compounds of formula I wherein $XR^4$ represents $NO_2$ and W represents COO, according to an analogous procedure described for the preparation of compounds of formula IIb.

Compounds of formula Xb may be prepared from compounds of formula Vb, representing compounds of formula I wherein $XR^4$ represents $NO_2$, W represents COO, and $R^2$ represents hydrogen, by reaction with an acid chloride forming agent such as $SOCl_2$ followed by reaction with an alcohol of formula XI, wherein $R^2$ is as defined for formula I, according to an analogous procedure described for the preparation of compounds of formula Xa.

Compounds of formula XIIb may be prepared from compounds of formula XIIIb, representing compounds of formula I wherein $XR^4$ represents $NO_2$ and W represents CO, according to an analogous procedure described for the preparation of compounds of formula IIb.

Compounds of formula XIIIb may be prepared from compounds of formula Vb, representing compounds of formula I wherein $XR^4$ represents $NO_2$, W represents COO, and $R^2$ represents hydrogen, by reaction in a suitable solvent with an organometallic compound of formula XIV, wherein $R^2$ is as defined for formula I and M represents a metal such as magnesium or preferably lithium, according to an analogous procedure described for the preparation of compounds of formula XIIIa.

Scheme III

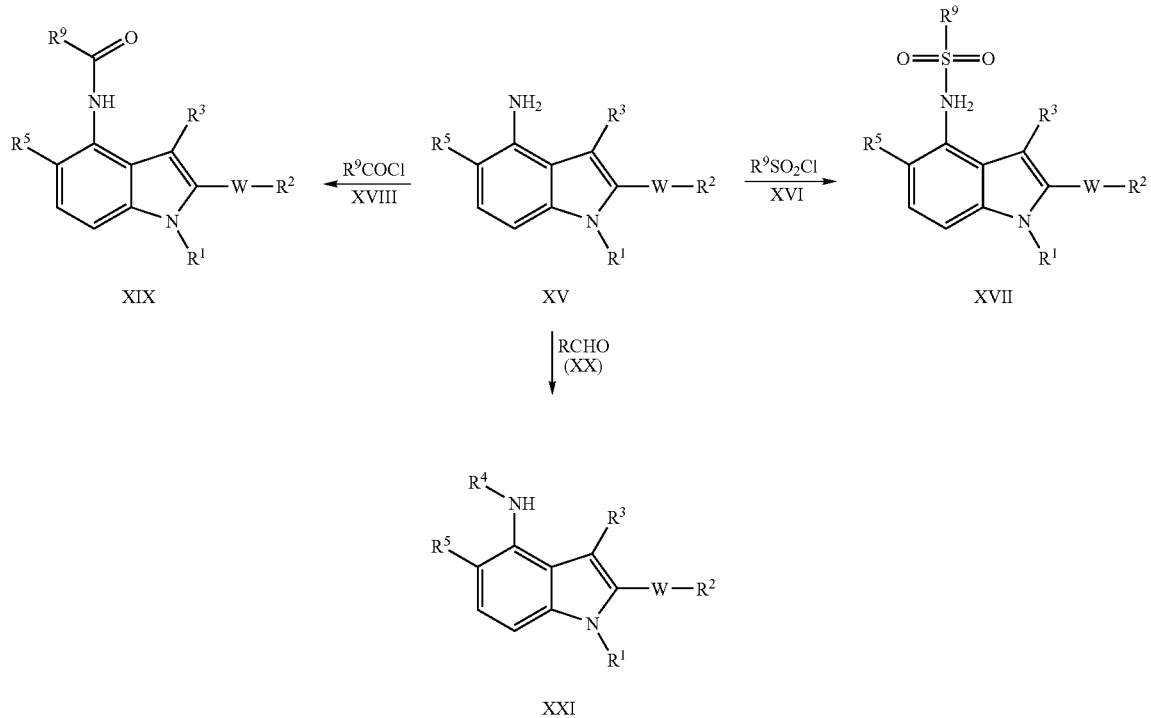

Scheme III outlines general methods for the preparation of compounds of formula I wherein X represents NH and $R^4$ represents $R^9SO_2$ (formula XVII), $R^9CO$ (formula XIX), or $R^4$ (formula XXI) from a common intermediate of formula XV wherein $XR^4$ represents $NH_2$. The other substituents, $R^1$, W, $R^2$, $R^3$ and $R^5$, are as defined for formula I. Compounds of formula XV may be prepared by methods outlined in Scheme II.

Compounds of formula XVII may be prepared from compounds of formula XV, representing compounds of formula I wherein $XR^4$ represents $NH_2$, by reaction with a sulfonyl chloride of formula XVI, wherein $R^9$ is as defined for formula I, in the presence of a suitable base and solvent. Suitable bases include DIEA, TEA, pyridine, $NaHCO_3$ and $Na_2CO_3$. Suitable solvents include THF, DCM, chloroform, benzene, toluene and EtOAc. The reaction is preferably performed at a temperature of 0-100° C. and most preferably at a temperature of 25-50° C. Compounds of formula XVI are either commercially available or may be prepared by methods known to one skilled in the art.

Compounds of formula XIX may be prepared from compounds of formula XV, representing compounds of formula I wherein $XR^4$ represents $NH_2$, by reaction with an acid chloride of formula XVIII, wherein $R^9$ is as defined for formula I, in the presence of a suitable base and solvent. Suitable bases include DIEA, TEA, pyridine, $NaHCO_3$ and $Na_2CO_3$. Suitable solvents include THF, DCM, chloroform, benzene, toluene and EtOAc. The reaction is preferably performed at a temperature of 0-100° C. and most preferably at ambient temperature. Compounds of formula XVIII are either commercially available or may be prepared by methods known to one skilled in the art.

Compounds of formula XXI may be prepared from compounds of formula XV, representing compounds of formula I wherein $XR^4$ represents $NH_2$, by reaction with an aldehyde of formula XX, wherein R represents $C_1$-$C_3$ alkyl, Ar, or $CH_2Ar$, in the presence of a suitable reducing agent and solvent. Suitable reducing agents include sodium borohydride, sodium cyanoborohydride, sodium triacetoxyborohydride, zinc and HCl, and hydrogen and a suitable catalyst. Suitable catalyst include platinum oxide or Raney nickel. Suitable solvents include EtOH, aqueous EtOH, water and THF. The reaction is preferably performed at a temperature of 20-100° C. and most preferably at ambient temperature. Compounds of formula XX are either commercially available or may be prepared by methods known to one skilled in the art.

Where necessary, hydroxy, amino or other reactive groups may be protected using a protecting group as described in the standard text, 'Protecting Groups in Organic Synthesis', $3^{rd}$ Edition, T. W. Greene and P. G. M. Wuts, 1999, J Wiley & Sons, Inc.

The above described reactions, unless otherwise noted, are usually conducted at a pressure of about one to about three atmospheres, preferably at ambient pressure (about one atmosphere).

Unless otherwise stated, the above described reactions are conducted under an inert atmosphere, preferably under a nitrogen atmosphere.

The compounds of the invention and intermediates may be isolated from their reaction mixtures by standard techniques.

Acid addition salts of the compounds of formula I which may be mentioned include salts of mineral acids, for example the hydrochloride and hydrobromide salts; and salts formed with organic acids such as formate, acetate, maleate, benzoate, tartrate, and fumarate salts. Acid addition salts of compounds of formula I may be formed by reacting the free base or a salt, enantiomer or protected derivative thereof, with one or more equivalents of the appropriate, acid. The reaction may be carried out in a solvent or medium in which the salt is insoluble or in a solvent in which the salt is soluble, e.g., water, dioxane, ethanol, tetrahydrofuran or diethyl ether, or a mixture of solvents, which may be removed in vacuum or by freeze drying. The reaction may be a metathetical process or it may be carried out on an ion exchange resin.

The compounds of formula I exist in tautomeric or enantiomeric forms, all of which are included within the scope of the invention. The various optical isomers may be isolated by separation of a racemic mixture of the compounds using conventional techniques, e.g., fractional crystallization, or chiral HPLC. Alternatively the individual enantiomers may be made by reaction of the appropriate optically active starting materials under reaction conditions which will not cause racemization.

The compounds of formula I, or an enantiomer thereof, and pharmaceutically acceptable salts thereof, may be used on their own or in the form of appropriate medicinal preparations for enteral or parenteral administration. According to a further aspect of the invention, there is provided a pharmaceutical composition including preferably less than 80% and more preferably less than 50% by weight of a compound of the invention in admixture with an inert pharmaceutically acceptable diluent or carrier.

Examples of diluents and carriers are:
for tablets and dragees: lactose, starch, talc, stearic acid;
for capsules: tartaric acid or lactose;
for injectable solutions: water, alcohols, glycerin, vegetable oils;
for suppositories: natural or hardened oils or waxes.

There is also provided a process for the preparation of such a pharmaceutical composition, which comprises mixing the ingredients.

It will be understood that a pharmaceutical composition comprising a positive modulator of a nicotinic receptor agonist together with a pharmaceutically acceptable carrier said positive modulator having the capability to increase the efficacy of the said receptor agonist. For the purposes of the present invention, the term "positive modulator" or "positive modulator of a nicotinic receptor agonist" shall be understood as a compound having the capability to increase the maximum efficacy of a nicotinic receptor agonist.

It will be understood that the invention includes compositions comprising either a positive modulator as the only active substance, thus modulating the activity of endogenous nicotinic receptor agonists, such as acetylcholine, or choline, or a positive modulator in combination with a nicotinic receptor agonist. Thus, the said pharmaceutical compositions containing a positive modulator of a nicotinic receptor agonist may, in addition comprise a nicotinic receptor agonist.

In a preferred form of the invention, the said nicotinic receptor agonist is an α7-nicotinic receptor agonist. Example of an α7-nicotinic receptor agonist is (−)-spiro[1-azabicyclo [2.2.2.]octane-3,5'-oxazolidine]-2'-one. Several α7-nicotinic receptor agonists are known in the art, e.g. from WO 96/06098, WO 97/30998 and WO 99/03859.

A further aspect of the invention provides a method for the treatment of a condition associated with reduced nicotine transmission, by administering to a patient in need of such treatment, a medically effective amount of a positive modulator of a nicotinic receptor agonist, said positive modulator having the capability to increase the efficacy of the said nicotinic receptor agonist.

It will be understood that the methods of treatment of this invention includes either a positive modulator as the only active substance, thus modulating the activity of endogenous nicotinic receptor agonists, such as acetylcholine or choline, or a positive modulator administered together with a nicotinic receptor agonist.

In another preferred form of the invention, the said method of treatment includes a nicotinic receptor agonist, which is an α7-nicotinic receptor agonist. Example of an α7-nicotinic receptor agonist is (−)-spiro[1-azabicyclo[2.2.2.]octane-3,5′-oxazolidine]-2′-one. Several α7-nicotinic receptor agonists are known in the art, e.g. from WO 96/06098, WO 97/30998 and WO 99/03859.

Utility

A further aspect of the invention is the use of compound according to the invention in the manufacture of a medicament for the treatment or prophylaxis of a condition associated with reduced nicotinic receptor transmission or a condition associated with reduced nicotinic density which could be one of the below mentioned diseases or conditions which comprises administering a therapeutically effective amount of compounds according to the invention to a patient.

It will be understood that the use includes compositions comprising either a positive modulator as the only active substance, thus modulating the activity of endogenous nicotinic receptor agonists, or a positive modulator in combination with a nicotinic receptor agonist. Thus, the said use of pharmaceutical compositions containing a positive modulator of a nicotinic receptor agonist may, in addition comprise a nicotinic receptor agonist.

In a preferred form of the invention, the use of the said nicotinic receptor agonist is represented by an α7-nicotinic receptor agonist. Example of an α7-nicotinic receptor agonist is (−)-spiro[1-azabicyclo[2.2.2.]octane-3,5′-oxazolidine]-2′-one. Several α7-nicotinic receptor agonists are known in the art, e.g. from WO 96/06098, WO 97/30998 and WO 99/03859.

Examples of diseases or conditions include schizophrenia, mania and manic depression, anxiety, Alzheimer's disease, learning deficit, cognition deficit, attention deficit, memory loss, Lewy Body Dementia, Attention Deficit Hyperactivity Disorder, Parkinson's disease, Huntington's disease, Tourette's syndrome, jetlag, and nicotine addiction (including that resulting from exposure to products containing nicotine).

It will be understood that the said positive modulator can be administered either with the purpose of acting on endogenous nicotine receptor agonists, or in combination with an exogenous nicotinic receptor agonist.

A further aspect of the invention relates to a compound for treating or preventing a condition or disorder as exemplified above arising from dysfunction of nicotinic acetylcholine receptor neurotransmission in a mammal, preferably a human, compositions comprising either a positive modulator as the only active substance, thus modulating the activity of endogenous nicotinic receptor agonists, or a positive modulator in combination with a nicotinic receptor agonist. Thus, the said use of pharmaceutical compositions containing a positive modulator of a nicotinic receptor agonist may, in addition comprise a nicotinic receptor agonist, effective in treating or preventing such disorder or condition and an inert pharmaceutically acceptable carrier.

Experimental Methods

The activity of the compounds of the invention may be measured in the tests set out below:

(a) *Xenopus oocyte* current recording

The *Xenopus oocyte* has provided a powerful means of assessing the function of proteins thought to be subunits of ligand-gated ion-channels. Injection of RNA transcribed from cDNA clones encoding the appropriate receptor subunits, or injection of cDNA in which the coding sequence is placed downstream of a promoter, results in the appearance of functional ligand-gated ion-channels on the surface of the oocyte (see e.g. Boulter et al. (1987) Proc. Natl. Acad. Sci. U.S.A. 84, 7763-7767).

Consequently, one convenient technique to assess the enhancement of nicotinic efficacy is two-electrode voltage-clamp recording from *Xenopus oocytes* expressing α7-nicotinic receptors from cRNA.

*Xenopus laevis* frogs (Xenopus I, Kalamazoo, Mich.) were anesthetized using 0.15% tricaine. Oocytes were removed to OR2 solution (82 mM NaCl, 2.5 mM KCl, 5 mM HEPES, 1.5 mM $NaH_2PO_4$, 1 mM $MgCl_2$, 0.1 mM EDTA; pH 7.4). The oocytes were defolliculated by incubation in 25 mL OR2 containing 0.2% collagenase 1A (Sigma) two times for 60 min on a platform vibrating at 1 Hz and stored in Leibovitz's L-15 medium (50 µg/mL gentomycin, 10 Units/mL penicillin, and 10 µg/mL streptomycin). Approximately 50 ng of cRNA was injected in each oocyte the following day. cRNA was synthesised from cDNA using Message Machine (purchased from Abion).

The external recording solution consisted of 90 mM NaCl, 1 mM KCl, 1 mM $MgCl_2$, 1 mM $BaCl_2$, 5 mM HEPES; pH 7.4. Two-electrode voltage-clamp recording was carried out using an Oocyte Clamp amplifier (OC 725C; Warner Instrument, Hamden, Conn.). Oocytes were impaled with two electrodes of 1-2 MΩ tip resistance when filled with 3 M KCl. Recordings were begun when membrane potential became stable at potentials negative to −20 mV (resting membrane potentials are less negative when $Ba^{++}$ replaces $Ca^{++}$ in bathing solutions). Membrane potential was clamped at −80 mV. ACh was purchased from Sigma. Oocytes were continuously perfused (5 mL/min) with recording solution with or without ACh.

Current amplitude was measured from baseline to peak. $EC_{50}$ values, maximal effect, and Hill slopes were estimated by fitting the data to the logistic equation using GraphPad Prism (GraphPad Software, Inc., San Diego, Calif.).

Increases in agonist efficacy elicited by a positive modulator can be calculated in two ways:

(1) As percent potentiation of current amplitude: which is defined as $100(I_m-I_c)/I_c$ where $I_m$ is current amplitude in the presence of modulator and $I_c$ is current in the absence of modulator.

(2) As percent potentiation of "area under curve" of an agonist trace: which is the integration of net current over time. Area under the curve is a common representation of the total ion flux through the channel.

(b) $Ca^{2+}$ flux imaging

Imaging of $Ca^{2+}$ flux through nAChR α7 receptors transiently expressed in a cell line is another means of assaying modulator activity.

Cells expressing α7 receptors (for example HEK-293 cells or cell cultured neurons) are grown to confluence in 96 well plates and loaded with fluo-3, a fluorescent calcium indicator. To screen for α7 modulatory activity, the 96 well plate is placed in a fluorescence imaging plate reader (FLIPR) and test compounds along with an α7 agonist are applied simultaneously to all wells. Receptor activation is measured by calcium influx into cells, which is quantified by the increase in fluorescence intensity of each well, recorded simultaneously by the FLIPR. A modulatory effect is determined by the increase in fluorescence over that of agonist alone. Similarly, to test for nAChR α7 agonist activity, test compounds along with an α7 modulator are applied simultaneously to all wells. Receptor activation is measured by calcium influx into cells which is quantified by the increase in fluorescence intensity of each well, recorded simultaneously by the FLIPR. An agonist effect is determined by the increase in fluorescence over that of modulator alone.

Cell-cultured neurons are prepared according to the following method: Eighteen day old Sprague-Dawley rat fetuses (E-18) were aseptically removed from the pregnant male, sacrificed, the frontal cortices of the brains removed, the meninges stripped, and the cleaned cortex placed into cold HBSS. If hippocampus was desired, the hippocampus was dissected away from the cortex and then placed into cold HBSS. The tissues were mechanically dispersed, washed once in HBSS (200 g for 30 minutes in 4° C.) resuspended in a modification of Sato's medium supplemented with glutamine, antibiotics, potassium chloride, insulin, transferrin, selenium, and 5% heat-inactivated fetal bovine serum (FBS; endotoxin free) and plated into each of a 24-well plate (coated with poly-L-lysine). The wells could contain glass coverslips which were also coated with PLL. The plates were incubated at 37° C. in a $CO_2$ incubator. After 24 hours the medium was removed, fresh medium added, and the cells allowed to grow for at least another 11 days, feeding when necessary.

The compounds of the invention are compounds, which causes a 100% potentiation (2-fold increase) of baseline current (as described above), as measured baseline to peak at low concentration of Acetylcholine (30 μM), indicating that they are expected to have useful therapeutic activity. The compounds of the invention are also compounds, which increase the flux of $Ca^{2+}$ when applied in the $Ca^{2+}$ flux-imaging assay, as described above. Any increase of $Ca^{2+}$ flux, caused by a compound of the invention, compared to the $Ca^{2+}$ flux casued by an agonist alone (as measured in Fluorescence Intensity Units) indicates that they are expected to have useful therapeutic activity.

The use of compounds of the invention have the advantage that they may be less toxic, be more efficacious, be longer acting, have a broader range of activity, be more potent, produce fewer side effects, are more easily absorbed or have other useful pharmacological properties.

General Experimental Procedures

Commercial reagents were used without further purification. Mass spectra were recorded following either chemical ionization (MS CI) or electrospray (MS ES) ionization methods and are reported as m/z for the protonated cationic parent molecular ion ($M^+$+H) or the deprotonated anionic parent molecular ion ($M^-$−H). Room temperature refers to 20-25° C.

EXAMPLES

The following examples are preferred non-limiting examples embodying preferred aspects of the invention.

Intermediate Examples

Example 1

Ethyl 4-benzyloxy-1-methyl-1H-indole-2-carboxylate

To a stirred suspension of sodium hydride (0.27 g, 60% dispersion in mineral oil) in DMF (50 mL) under nitrogen at room temperature was added ethyl 4-benzyloxyindole-2-carboxylate (1.59 gm). Methyl iodide (0.5 mL) was added 10 min. later. After 2 hr. excess sodium hydride was quenched with acetic acid (0.4 mL) and the solvent evaporated under reduced pressure. The residue was taken into EtOAc, washed with water and brine, dried over $MgSO_4$, and evaporated to dryness to give an oil which was triturated with hexane to precipitate 1.45 g of the title compound. Mp 89-90.5° C.

Example 2

4-Benzyloxy-1-methyl-1H-indole-2-carboxylic acid

To a stirred solution of ethyl 4-benzyloxy-1-methyl-1H-indole-2-carboxylate (3.09 g) in THF (200 mL) was added $LiOH.H_2O$ (1.26 g) in water (200 mL) and the resulting two phase solution was heated at 45° C. under nitrogen overnight. The cooled reaction mixture was evaporated to remove THF and the remaining aqueous solution was acidified with $NaHSO_4$ to precipitate the title compound, which was collected, washed with water, and dried to give 2.87 g of the title compound. Mp 216.6-216.8° C.

Example 3

4-Benzyloxy-1-methyl-1H-indole-2-carbonyl chloride

To a stirred suspension of 4-benzyloxy-1-methyl-1H-indole-2-carboxylic acid (0.75 g) in benzene (5 mL) was added thionyl chloride (2.8 mL) in benzene (5 mL) followed by heated at 80° C. for 45 min. to give a clear orange solution. Evaporation to dryness gave 0.80 g of the title compound as an orange solid, which was used without further purification.

Example 4

1-Fluoromethyl-2-phenylethyl methanesulfonate

To a stirred solution of 1-fluoromethyl-2-phenylethanol (1.0 g, prepared as described by Bergmann, et al., J. Chem. Soc., 1961, 3448-3452) in DCM (30 mL) at 0° C. under nitrogen was added triethylamine (1.36 mL) followed by dropwise addition of methanesulfonyl chloride (0.6 mL). The mixture was allowed to slowly warm to room temperature overnight. The reaction mixture was poured into water and extracted with EtOAc. The EtOAc extracts were washed with water and brine, dried over $Na_2SO_4$, and concentrated to dryness to give 1.3 g of the title compound. MS CI, ($M^+$+H)= 233, ($M^+$+H −$CH_3SO_3H$)=138.

Example 5

(2-Azido-3-fluoro-propyl)benzene

To a stirred solution of 1-fluoromethyl-2-phenylethyl methanesulfonate (1.1 g) in anhydrous DMF (15 mL) under nitrogen was added sodium azide (0.53 g) followed by heating at 80° C. overnight. The cooled reaction mixture was diluted with equal parts of water and brine and extracted with EtOAc. The extracts were washed with water and brine, dried over $Na_2SO_4$, and concentrated to an oil which was chromatographed over silica gel with a mixture of EtOAc and hexane to give 0.70 g of the title compound. MS ES ($M^+$+H−$N_2$) 151.

Example 6

1-Fluoromethyl-2-phenylethylamine

To a solution of (2-azido-3-fluoro-propyl)benzene (0.6 g) in MeOH (50 mL) was added 10% Pd/C catalyst and the suspension was hydrogenated for 2 hr. at 3 atmospheres pressure. The filtered reaction mixture and MeOH washings were concentrated to an oil which was chromatographed over silica gel with an ammoniated mixture of MeOH/ether (1:9) to give 0.38 g of the title compound. MS ES (M$^+$+H)=154.

Example 7

(R)-N-(2-Fluoro-3-phenylpropyl)-4-methylbenzenesulfonamide

To a stirred solution of hydrogen fluoride-pyridine (13 mL) at 0° C. under nitrogen was added (S)-(+)-2-benzyl-1-(p-tolylsulfonyl)aziridine (2 g) in one portion. The cooling bath was removed briefly until reaction became exothermic and then returned. After an additional 5 min. the reaction mixture was poured onto 100 mL of cracked ice. The product was extracted into ether, washed carefully with saturated NaHCO$_3$ and brine, dried over Na$_2$SO$_4$, and evaporated to a white solid. The solid was triturated with hexane, collected and washed with ether/hexane to give 1.7 g of the title compound. Mp 130-133° C.; MS ES (M$^+$+H)=308.

Example 8

(R)-2-Fluoro-3-phenylpropylamine

To a two necked flask equipped with a dry ice condenser was added (R)-N-(2-Fluoro-3-phenylpropyl)-4-methylbenzenesulfonamide (1.0 g) and ammonia gas to condense about 25 mL of liquid. Small pieces of sodium were added to the stirred solution until a dark orange color persisted for 5 min. Methanol was added to quench the reaction. After evaporation of the ammonia the product was dissolved in MeOH, filtered, and concentrated. The residue was extracted into chloroform and chromatographed over silica gel with an ammoniated mixture of MeOH/ether (1:19) to give 0.14 g of the title compound as an oil. MS ES (M$^+$+H-NH$_3$)=136.

Compound Examples:

Example 9

Ethyl 4-hydroxy-1-methyl-1H-indole-2-carboxylate

To 10% Pd/C (0.13 g) in EtOH (250 mL) was added ethyl 4-benzyloxy-1-methyl-1H-indole-2-carboxylate (1.33 g) and the suspension was shaken overnight under a hydrogen pressure of 3 atmospheres at room temperature. The residue left on evaporation of the filtered reaction mixture was chromatographed over silica gel with a mixture of EtOAc and hexane to give 0.43 g of the title compound. MS ES (M$^+$+H)=220.

Example 10

4-Hydroxy-1-methyl-1H-indole-2-carboxylic acid

To a solution of ethyl 4-hydroxy-1-methyl-1H-indole-2-carboxylate (0.20 g) in THF (20 mL) was added LiOH.H$_2$O (0.1 g) in water (20 mL) and the resulting two phase solution was stirred at room temperature under nitrogen for 4 hr. The reaction mixture was acidified with KHSO$_4$ and the product was extracted into EtOAc, washed with brine, dried over MgSO$_4$, and concentrated. The residue was chromatographed over silica gel with a mixture of EtOAc and hexane to give 0.12 g of the title compound. MS ES (M$^+$+H)=192.

Example 11

N-Phenethyl 4-hydroxy-1-methyl-1H-indole-2-carboxamide

To a solution of 4-benzyloxy-1-methyl-1H-indole-2-carboxylic acid (0.20 g) in DMF (10 mL) was added TBTU (0.23 g), HOBt (0.11 g) and DIEA (0.27 mL). After 5 min., phenethylamine (0.11 mL) was added and stirring was continued overnight under nitrogen at room temperature. The residue remaining after DMF evaporation was dissolved in EtOAc; washed with dilute HCl, saturated NaHCO$_3$, and brine; dried over MgSO$_4$; and concentrated at reduced pressure to give the intermediate product N-phenethyl 4-benzyloxy-1-methyl-1H-indole-2-carboxyamide (0.18 g) which was used without further purification. Hydrogenation of this product by a method analogous to that described in Example 9 give 0.14 g of the title compound.
MS CI (M$^+$+H)=295.

Example 12

N-Methyl-N-Phenethyl 4-hydroxy-1-methyl-1H-indole-2-carboxamide

From 4-benzyloxy-1-methyl-1H-indole-2-carboxylic acid and N-methylphenethylamine the title compound was prepared by a method analogous to that described in Example 11. MS ES (M$^+$+H)=309.

Example 13

N-(4-Dimethylaminobenzyl) 4-hydroxy-1-methyl-1H-indole-2-carboxamide

To a solution of 4-hydroxy-1-methyl-1H-indole-2-carboxylic acid (Example 10, 0.12 g) in DMF (10 mL) was added TBTU (0.20 g), HOBt (0.10 g) and DIEA (0.35 mL). After 5 min., 4-(dimethylamino)benzylamine dihydrochloride (0.14 g) was added and stirring was continued overnight under nitrogen at room temperature. The residue remaining after DMF evaporation was purified by reversed phased chromatography on C$_{18}$ silica with a trifluoroacetic acid (0.025%) acidified acetonitrile water gradient to give 0.14 g of the title compound. MS ES (M$^+$+H)=324.

Example 14

N-(4-Chlorobenzyl) 4-hydroxy-1-methyl-1H-indole-2-carboxamide

From 4-benzyloxy-1-methyl-1H-indole-2-carboxylic acid and 4-chlorobenzylamine the title compound was prepared by a method analogous to that described in Example 11. MS ES (M$^+$+H)=315 and 317.

Example 15

N-Benzyl 4-hydroxy-1-methyl-1H-indole-2-carboxamide

From 4-benzyloxy-1-methyl-1H-indole-2-carboxylic acid and benzylamine the title compound was prepared by a method analogous to that described in Example 11. MS ES (M$^+$+H)=281.

Example 16

N-(4-Phenylbutyl) 4-hydroxy-1-methyl-1H-indole-2-carboxamide

From 4-benzyloxy-1-methyl-1H-indole-2-carboxylic acid and 4-phenylbutylamine the title compound was prepared by a method analogous to that described in Example 11. MS ES (M$^+$+H)=323.

Example 17

N-(3-Phenylpropyl) 4-hydroxy-1-methyl-1H-indole-2-carboxamide

From 4-benzyloxy-1-methyl-1H-indole-2-carboxylic acid and 3-phenylpropylamine the title compound was prepared by a method analogous to that described in Example 11. MS ES (M$^+$+H)=309.

Example 18

N-Phenyl 4-hydroxy-1-methyl-1H-indole-2-carboxamide

From 4-benzyloxy-1-methyl-1H-indole-2-carboxylic acid and aniline the title compound was prepared by a method analogous to that described in Example 11. MS ES (M$^+$+H)=267.

Example 19

N-(4-Chlorophenyl) 4-hydroxy-1-methyl-1H-indole-2-carboxamide

From 4-benzyloxy-1-methyl-1H-indole-2-carboxylic acid and 4-chloroaniline the title compound was prepared by a method analogous to that described in Example 11. MS ES (M$^+$+H)=301 and 303.

Example 20

N-(3-Biphenyl) 4-hydroxy-1-methyl-1H-indole-2-carboxamide

From 4-benzyloxy-1-methyl-1H-indole-2-carboxylic acid and 3-aminobiphenyl the title compound was prepared by a method analogous to that described in Example 11. MS ES (M$^+$+H)=343.

Example 21

N-Ethyl 4-hydroxy-1-methyl-1H-indole-2-carboxamide

From 4-benzyloxy-1-methyl-1H-indole-2-carboxylic acid and ethylamine the title compound was prepared by a method analogous to that described in Example 11. MS ES (M$^+$+H)=219.

Example 22

4-Hydroxy-1-methyl-2-(pyrrolidin-1-ylcarbonyl)-1H-indole

From 4-benzyloxy-1-methyl-1H-indole-2-carboxylic acid and pyrrolidine the title compound was prepared by a method analogous to that described in Example 11. MS ES (M$^+$+H)=245.

Example 23

N-(1-Fluoromethyl-2-phenylethyl) 4-hydroxy-1-methyl-1H-indole-2-carboxamide

To a solution of 1-fluoromethyl-2-phenylethylamine (0.38 g) in DCM (5 mL) at 0° C. under nitrogen was add 4 benzyloxy-1-methyl-1H-indole-2-carbonyl chloride (0.37 g) in DCM (5 mL) followed by slow warming to room temperature over 2 hr. The reaction mixture was concentrated to half volume and partitioned between EtOAc and water. The organic layer was washed with water and brine, dried over Na$_2$SO$_4$, and concentrated to a residue which was triturated with ether to give 0.32 g of the intermediate compound N-(1-fluoromethyl-2-phenylethyl) 4-benzyloxy-1-methyl-1H-indole-2-carboxamide: mp 172-173° C.; MS ES (M$^+$+H)=417. Hydrogenation of this intermediate (0.26 g) by a method analogous to that described in Example 9 gave 0.12 g of the title compound. Mp 163.5-165.5° C.; MS ES (M$^+$+H)=327.

Example 24

(R)-N-(2-Hydroxy-1-phenylethyl) 4-hydroxy-1-methyl-1H-indole-2-carboxamide

From (R)-2-hydroxy-1-phenylethylamine and 4 benzyloxy-1-methyl-1H-indole-2-carbonyl chloride the title compound was prepared by a method analogous to that described in Example 23. MS ES (M$^+$+H)=311.

Example 25

(S)-N-(2-Azido-1-benzylethyl)-4-hydroxy-1-methyl-1H-indole-2-carboxamide

From (S)-2-azido-1-benzylethylamine (prepared as described by Horwell, et al., J. Med. Chem., 1991, 404-414) and 4 hydroxy-1-methyl-1H-indole-2-carboxylic acid the title compound was prepared by a method analogous to that described in Example 23. MS ES (M$^+$+H)=350.

Example 26

N-(2-Fluoroethyl)-4-hydroxy-1-methyl-1H-indole-2-carboxamide

From 2-fluoroethylamine and 4 benzyloxy-1-methyl-1H-indole-2-carbonyl chloride the title compound was prepared by a method analogous to that described in Example 23. MS ES (M$^-$−H)=235.

Example 27

(R)-N-(2-Fluoro-3-phenylpropyl)-4-hydroxy-1-methyl-1H-indole-2-carboxamide

From (R)-2-fluoro-3-phenylpropylamine and 4 benzyloxy-1-methyl-1H-indole-2-carbonyl chloride the title compound was prepared by a method analogous to that described in Example 23. MS ES (M$^+$+H)=327.

Example 28

Resolution of Example 23

(−)-N-(1-Fluoromethyl-2-phenylethyl) 4-hydroxy-1-methyl-1H-indole-2-carboxamide

Chiral chromatography of Example 23 (40 mg) on a Chiralpak® AD column (Chiral Technologies, Inc., 5×50 cm, 20 μ) in isopropyl alcohol/hexanes/diethylamine (40:59:1) at 40 mL/min with UV (238 nM) monitoring gave two peaks. The faster eluting peak was isolated to give 12 mg of the title compound as a white solid. MS ES (M⁺+H)=327; M.P. 161-162° C.; [α]$_D$=−158.6° (MeOH, C=1; 99.6% ee by chiral HPLC).

Example 29

Resolution of Example 23

(+)-N-(1-Fluoromethyl-2-phenylethyl) 4-hydroxy-1-methyl-1H-indole-2-carboxamide

The slower eluting peak from Example 28 was isolated to give 12 mg of material which was chromatographed on silica gel with EtOAc/hexanes (1:4) to give 8.8 mg of the title compound. MS ES (M⁺+H)=327; M.P. 157-158° C.; [α]$_D$=+141° (MeOH, C=1; 96.2% ee by chiral HPLC).

Example 30

(R)-N-(2-Azido-1-benzylethyl)-4-hydroxy-1-methyl-1H-indole-2-carboxamide

From (R)-2-azido-1-benzylethylamine (prepared as described by Horwell, et al., J. Med. Chem., 1991, 404-414) and 4 hydroxy-1-methyl-1H-indole-2-carboxylic acid the title compound was prepared by a method analogous to that described in Example 13. MS ES (M⁺+H)=350; [α]$_D$=+94.8° (MeOH, C=1).

Example 31

(S)-N-(2-Cyano-1-benzylethyl)-4-hydroxy-1-methyl-1H-indole-2-carboxamide

From (S)-2-cyano-1-benzylethylamine (prepared by an adaptation of a method described by Caputo, et al., Tetrahedron, 1995, 12337-12350) and 4 hydroxy-1-methyl-1H-indole-2-carboxylic acid the title compound was prepared by a method analogous to that described in Example 13. MS ES (M⁺+H)=334; [α]$_D$=−110.8° (MeOH, C=1).

Example 32

Methyl (S)-2-{[(4-hydroxy-1-methyl-1H-indol-2-yl)carbonyl]amino}-3-phenylpropano-ate From L-phenylalanine methyl ester hydrochloride and 4 hydroxy-1-methyl-1H-indole-2-carboxylic acid the title compound was prepared by a method analogous to that described in Example 13. MS ES (M⁺+H)=353.

Example 33

N-(1-phenyl-3-butynyl)-4-hydroxy-1-methyl-1H-indole-2-carboxamide

From 1-phenyl-3-butyn-1-amine (Leboutet, et al., J Organomet Chem, 1991, 155-161) and 4 hydroxy-1-methyl-1H-indole-2-carboxylic acid the title compound was prepared by a method analogous to that described in Example 13. MS ES (M⁺+H)=319.

Example 34

(S)-N-[2-Azido-1-(4-methoxybenzyl)ethyl]-4-hydroxy-1-methyl-1H-indole-2-carbox-amide From (S)-1-azido-3-(4-methoxyphenyl)-2-propanamine [prepared by an adaptation of a method described by Horwell, et al., J. Med. Chem., 1991, 404-414 from (S)-2-amino-3-(4-methoxyphenyl)-1-propanol (prepared from O-methyl-L-tyrosine by an adaptation of a method described by Sutherland, et al., J Org Chem, 1998, 7764-7769] and 4 hydroxy-1-methyl-1H-indole-2-carboxylic acid the title compound was prepared by a method analogous to that described in Example 13. MS ES (M⁺+H)=380.

Example 35

(S)-N-[1-benzyl-2-hydroxyethyl]-4-hydroxy-1-methyl-1H-indole-2-carboxamide

From (S)-2-amino-3-phenylpropan-1-ol and 4-benzyloxy-1-methyl-1H-indole-2-carbonyl chloride the intermediate compound (S)-N-[1-benzyl-2-hydroxyethyl]-4-(benzyloxy)-1-methyl-1H-indole-2-carboxamide was prepared by a method analogous to that described in Example 23.

MS ES (M⁺+H)=415. Hydrogenation of this intermediate by a method analogous to that described in Example 9 gave the title compound. MS ES (M⁺+H)=325.

Example 36

2-[(4S)-4-benzyl-4,5-dihydro-1,3-oxazol-2-yl]-1-methyl-1H-indol-4-ol

To an ice chilled solution of (S)-N-[1-benzyl-2-hydroxyethyl]-4-(benzyloxy)-1-methyl-1H-indole-2-carboxamide (0.6 g) in benzene (25 mL) was added slowly a solution of thionyl chloride (1 mL) in benzene (5 mL). The ice bath was removed and the reaction mixture allowed to warm to room temperature over 2 h. Concentration of the reaction mixture in vacuo gave a solid which was washed with cold benzene and dried yielding 0.35 g of the intermediate 2-[(4S)-4-benzyl-4,5-dihydro-1,3-oxazol-2-yl]-4-(benzyloxy)-1-methyl-1H-indole hydrochloride. MS ES (M⁺+H)=397. The free base of this intermediate was hydrogenated by a method analogous to that described in Example 9 to give 0.25 g of the title compound. MS ES (M⁺+H)=307.

Example 37

2-[(4R)-4-benzyl-4,5-dihydro-1,3-oxazol-2-yl]-1-methyl-1H-indol-4-ol

From (R)-N-[1-benzyl-2-hydroxyethyl]-4-(benzyloxy)-1-methyl-1H-indole-2-carboxamide the title compound was prepared by a method analogous to that described in Example 36. MS ES (M⁺+H)=307.

The invention claimed is:
1. A compound of Formula I:

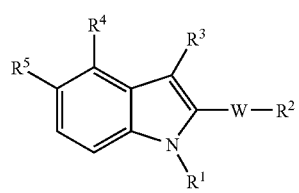

I wherein:
R¹ represents hydrogen or $C_1$-$C_4$alkyl;
W represents C(O)NR⁶;
R² represents $(CH_2)_pCH[(CH_2)_qR^7](CH_2)_rR^8$;

R$^3$ and R$^5$ independently represent hydrogen or C$_1$-C$_4$alkyl;
R$^4$ represents hydrogen or C$_1$-C$_4$alkyl;
R$^6$ represents hydrogen or C$_1$-C$_4$alkyl;
R$^7$ is Ar;
R$^8$ is selected from CN, N$_3$, or OR$^{10}$, where R$^{10}$ is H;
Ar represents phenyl or naphthyl;
Ar is optionally substituted with one or more substituents independently selected from:
hydrogen, halogen, C$_1$-C$_4$alkyl, CN, NO$_2$, CF$_3$, OR$^{12}$, NR$^{12}$R$^{13}$ and COOR$^{12}$;
R$^{12}$ and R$^{13}$ independently represent hydrogen, C$_1$-C$_4$alkyl, aryl, or heteroaryl, and
p, q, and t are independently 0, 1 or 2;
or an enantiomer thereof, or a pharmaceutically-acceptable salt thereof.

2. A compound according to claim 1, wherein:
R$^1$ represents hydrogen or methyl;
R$^4$ represents hydrogen or methyl, and
R$^3$ and R$^5$ each represent hydrogen;
or an enantiomer thereof, or a pharmaceutically-acceptable salt thereof.

3. A compound according to claim 1, wherein:
R$^1$, R$^3$, R$^4$ and R$^5$ are all hydrogen;
or an enantiomer thereof, or a pharmaceutically-acceptable salt thereof.

4. A compound according to claim 1, wherein:
R$^1$ is C$_1$-C$_4$alkyl;
R$^2$ is (CH$_2$)$_p$CH[(CH$_2$)$_q$R$^7$](CH$_2$)$_t$R$^8$ wherein p is 0, and q and t are each 1;
R$^3$, R$^4$ and R$^5$ are all hydrogen;
or an enantiomer thereof, or a pharmaceutically-acceptable salt thereof.

5. A compound according to claim 1, wherein Ar is phenyl, or an enantiomer thereof, or a pharmaceutically-acceptable salt thereof.

6. A compound selected from:
(R)-N-(2-hydroxy-1-phenylethyl) 4-hydroxy-1-methyl-1H-indole-2-carboxamide;
(S)-N-(2-azido-1-benzylethyl)-4-hydroxy-1-methyl-1H-indole-2-carboxamide;
(R)-N-(2-azido-1-benzylethyl)-4-hydroxy-1-methyl-1H-indole-2-carboxamide;
N-(1-phenyl-3-butynyl)-4-hydroxy-1-methyl-1H-indole-2-carboxamide;
(S)-N-[2-azido-1-(4-methoxybenzyl)ethyl]-4-hydroxy-1-methyl-1H-indole-2-carbox-amide, and
(S)-N-[1-benzyl-2-hydroxyethyl]-4-hydroxy-1-methyl-1H-indole-2-carboxamide,
or an enantiomer thereof, or a pharmaceutically-acceptable salt thereof.

7. A pharmaceutical composition comprising a compound according to any one of claims 1, 2, 3, 4, 5 or 6 in admixture with an inert pharmaceutically-acceptable diluent or carrier.

8. A pharmaceutical composition according to claim 7, additionally comprising a nicotinic receptor agonist.

* * * * *